(12) United States Patent
Hoseit et al.

(10) Patent No.: US 9,486,143 B2
(45) Date of Patent: Nov. 8, 2016

(54) INTRAVASCULAR FORWARD IMAGING DEVICE

(71) Applicant: VOLCANO CORPORATION, San Diego, CA (US)

(72) Inventors: Paul Hoseit, El Dorado Hills, CA (US); Paul Douglas Corl, Palo Alto, CA (US)

(73) Assignee: VOLCANO CORPORATION, San Diego, CA (US)

( * ) Notice: Subject to any disclaimer, the term of this patent is extended or adjusted under 35 U.S.C. 154(b) by 143 days.

(21) Appl. No.: 14/136,627

(22) Filed: Dec. 20, 2013

(65) Prior Publication Data

US 2014/0180135 A1    Jun. 26, 2014

Related U.S. Application Data

(60) Provisional application No. 61/745,358, filed on Dec. 21, 2012.

(51) Int. Cl.
| | | |
|---|---|---|
| *A61B 5/00* | (2006.01) | |
| *A61B 5/02* | (2006.01) | |
| *A61B 5/0215* | (2006.01) | |
| *A61B 8/08* | (2006.01) | |
| *A61B 8/12* | (2006.01) | |

(52) U.S. Cl.
CPC ........... *A61B 5/0084* (2013.01); *A61B 5/0095* (2013.01); *A61B 5/02007* (2013.01); *A61B 5/0066* (2013.01); *A61B 5/02152* (2013.01); *A61B 5/6851* (2013.01); *A61B 8/0891* (2013.01); *A61B 8/12* (2013.01)

(58) Field of Classification Search
CPC A61B 5/0066; A61B 5/0084; A61B 5/0095; A61B 5/02007; A61B 5/02152; A61B 5/6851; A61B 8/0891; A61B 8/12
See application file for complete search history.

(56) References Cited

U.S. PATENT DOCUMENTS

| | | |
|---|---|---|
| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |

(Continued)

FOREIGN PATENT DOCUMENTS

| | | |
|---|---|---|
| EP | 1041373 A2 | 10/2000 |
| EP | 01172637 A1 | 1/2002 |

(Continued)

OTHER PUBLICATIONS

Little et al., 1991, The underlying coronary lesion in myocardial infarction:implications for coronary angiography, Clinical Cardiology, 14(11):868-874.

(Continued)

*Primary Examiner* — Ruth S Smith
(74) *Attorney, Agent, or Firm* — Brown Rudnick LLP; Thomas C. Meyers

(57) ABSTRACT

The present invention generally relates to forward imaging devices for imaging the inside of a vessel and associated methods. The invention can involve an elongated body configured to fit within the vessel of a lumen and at least one imaging sensor located on the elongated body configured to image an object in a forward direction.

6 Claims, 12 Drawing Sheets

(56) References Cited

U.S. PATENT DOCUMENTS

| | | |
|---|---|---|
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |

(56) References Cited

U.S. PATENT DOCUMENTS

| | | |
|---|---|---|
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,485,413 B1 * | 11/2002 | Boppart et al. ............... 600/160 |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |

(56) References Cited

U.S. PATENT DOCUMENTS

| | | |
|---|---|---|
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B2 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |

(56) References Cited

U.S. PATENT DOCUMENTS

| | | |
|---|---|---|
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |

(56) References Cited

U.S. PATENT DOCUMENTS

| | | |
|---|---|---|
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |

(56) References Cited

U.S. PATENT DOCUMENTS

| | | |
|---|---|---|
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0009694 A1* | 1/2011 | Schultz et al. ............... 600/109 |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |

(56) References Cited

U.S. PATENT DOCUMENTS

| | | |
|---|---|---|
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0046167 A1* | 2/2013 | Shah ............... A61B 8/0883 600/407 |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0123616 A1* | 5/2013 | Merritt ............ A61B 5/7445 600/427 |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |
| 2014/0323859 A1* | 10/2014 | Sarna ............... A61L 27/14 600/425 |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/44296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/066875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/006886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |

(56) References Cited

FOREIGN PATENT DOCUMENTS

| | | |
|---|---|---|
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, by-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome—strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope—Less Configurations with Application in Optical Coherence Tomography, Optics Letters 33(15):1741-1743.
Nissen, 2001, Coronary Angiography and Intravascular Ultrasound, American Journal of Cardiology, 87 (suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filed May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.

Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26 (1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4)1 547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, an FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vase Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
International Search Report and Written Opinion mailed Nov. 2, 2012, for International Patent Application No. PCT/US12/53168, filed Aug. 30, 2013 (8 pages).

(56) References Cited

OTHER PUBLICATIONS

International Search Report and Written Opinion mailed on Apr. 14, 2014, for International Patent Application No. PCT/US2013/076148, filed Dec. 18, 2013 (8 pages).
International Search Report and Written Opinion mailed on Apr. 21, 2014, for International Patent Application No. PCT/US2013/076015, filed Dec. 18, 2013 (7 pages).
International Search Report and Written Opinion mailed on Apr. 23, 2014, for International Patent Application No. PCT/US2013/075328, filed Dec. 16, 2013 (8 pages).
International Search Report and Written Opinion mailed on Apr. 29, 2014, for International Patent Application No. PCT/US13/76093, filed Dec. 18, 2013 (6 pages).
International Search Report and Written Opinion mailed on Apr. 9, 2014, for International Patent Application No. PCT/US13/75089, filed Dec. 13, 2013 (7 pages).
International Search Report and Written Opinion mailed on Feb. 21, 2014, for International Patent Application No. PCT/US13/76053, filed Dec. 18, 2013 (9 pages).
International Search Report and Written Opinion mailed on Feb. 21, 2014, for International Patent Application No. PCT/US2013/076965, filed Dec. 20, 2013 (6 pages).
International Search Report and Written Opinion mailed on Feb. 27, 2014, for International Patent Application No. PCT/US13/75416, filed Dec. 16, 2013 (7 pages).
International Search Report and Written Opinion mailed on Feb. 28, 2014, for International Patent Application No. PCT/US13/75653, filed Dec. 17, 2013 (7 pages).
International Search Report and Written Opinion mailed on Feb. 28, 2014, for International Patent Application No. PCT/US13/75990, filed Dec. 18, 2013 (7 pages).
International Search Report and Written Opinion mailed on Jan. 16, 2009, for International Patent Application No. PCT/US08/78963 filed on Oct. 6, 2008 (7 Pages).
International Search Report and Written Opinion mailed on Jul. 30, 2014, for International Patent Application No. PCT/US14/21659, filed Mar. 7, 2014 (15 pages).
International Search Report and Written Opinion mailed on Mar. 10, 2014, for International Patent Application No. PCT/US2013/076212, filed Dec. 18, 2013 (8 pages).
International Search Report and Written Opinion mailed on Mar. 11, 2014, for International Patent Application No. PCT/US13/76173, filed Dec. 16, 2013 (9 pages).
International Search Report and Written Opinion mailed on Mar. 11, 2014, for International Patent Application No. PCT/US13/76449, filed Dec. 19, 2013 (9 pages).
International Search Report and Written Opinion mailed on Mar. 18, 2014, for International Patent Application No. PCT/US2013/076502, filed Dec. 19, 2013 (7 pages).
International Search Report and Written Opinion mailed on Mar. 18, 2014, for International Patent Application No. PCT/US2013/076788, filed Dec. 20, 2013 (7 pages).
International Search Report and Written Opinion mailed on Mar. 19, 2014, for International Patent Application No. PCT/US13/75349, filed Dec. 16, 2013 (10 pages).
International Search Report and Written Opinion mailed on Mar. 19, 2014, for International Patent Application No. PCT/US2013/076587, filed Dec. 19, 2013 (10 pages).
International Search Report and Written Opinion mailed on Mar. 19, 2014, for International Patent Application No. PCT/US2013/076909, filed Dec. 20, 2013 (7 pages).
International Search Report and Written Opinion mailed on Mar. 7, 2014, for International Patent Application No. PCT/US2013/076304, filed Dec. 18, 2013 (9 pages).
International Search Report and Written Opinion mailed on Mar. 7, 2014, for International Patent Application No. PCT/US2013/076480, filed Dec. 19, 2013 (8 pages).
International Search Report and Written Opinion mailed on Mar. 7, 2014, for International Patent Application No. PCT/US2013/076512, filed Dec. 19, 2013 (8 pages).
International Search Report and Written Opinion mailed on Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Sihan et al., 2008, A novel approach to quantitative analysis of intraluminal optical coherence tomography imaging, Comput. Cardiol:1089-1092.

(56) References Cited

OTHER PUBLICATIONS

Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferonnetry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60 (9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18 (17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12 (24):6033-6039.
Zitova et al., 2003, Image registration methods: A survey. Image and Vision Computing, 21(11):977-1000.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.

(56) References Cited

OTHER PUBLICATIONS

Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61 (1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion mailed Mar. 11, 2014, for International Patent Application No. PCT/US13/75675, filed Dec. 17, 2013 (7 pages).
International Search Report and Written Opinion mailed Mar. 19, 2014, for International Patent Application No. PCT/US13/075353, filed Dec. 16, 2013 (8 pages).

\* cited by examiner

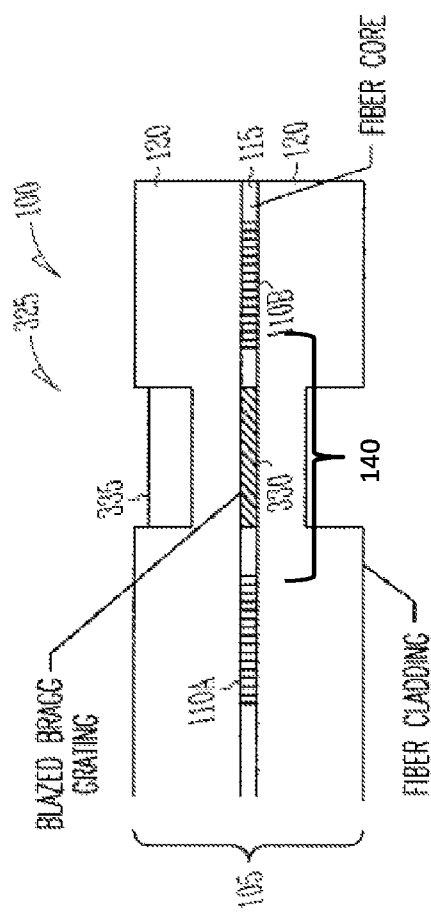
FIG. 6
--Prior Art--
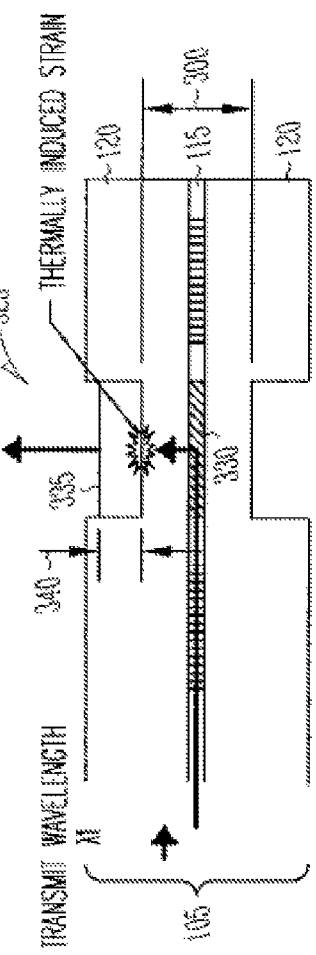
FIG. 7  --Prior Art--

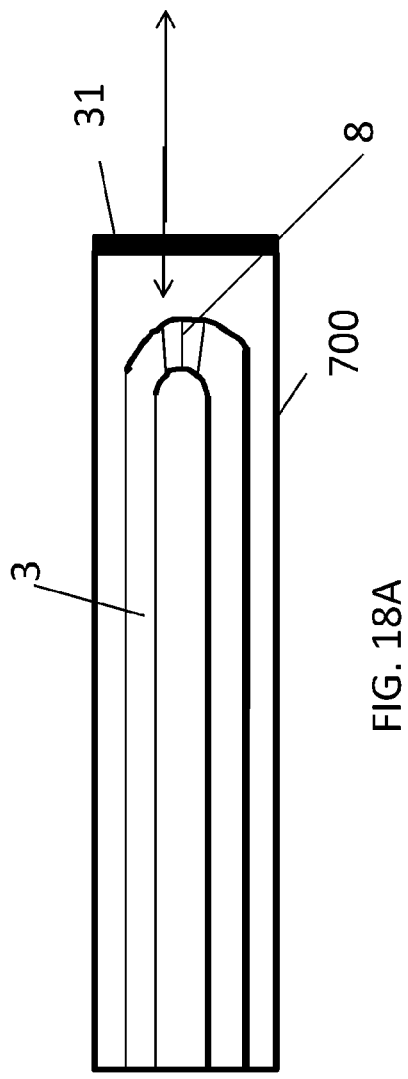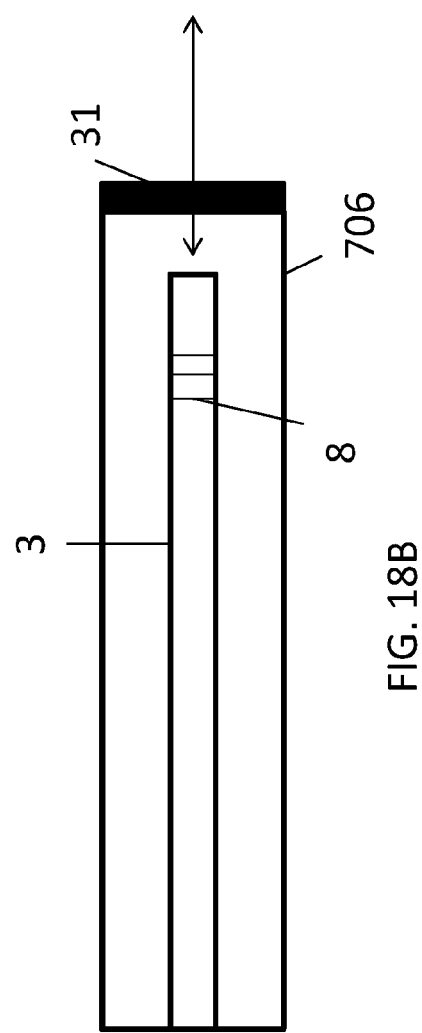

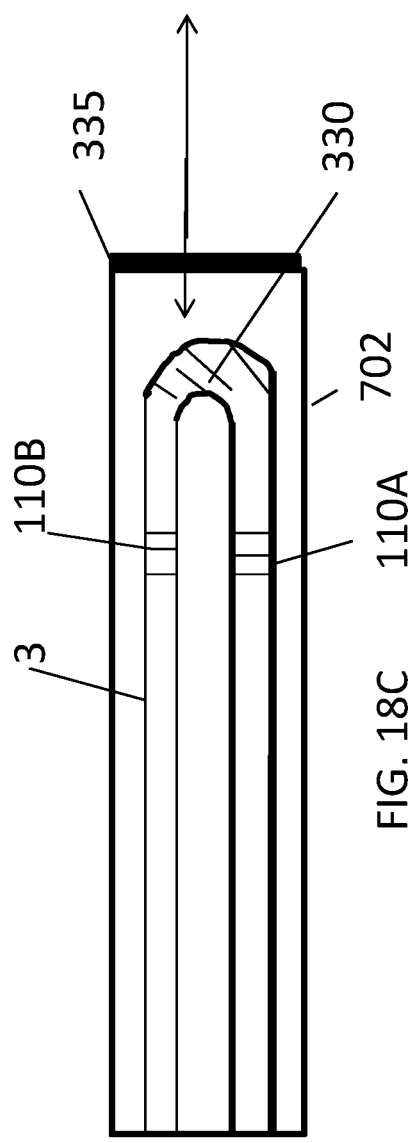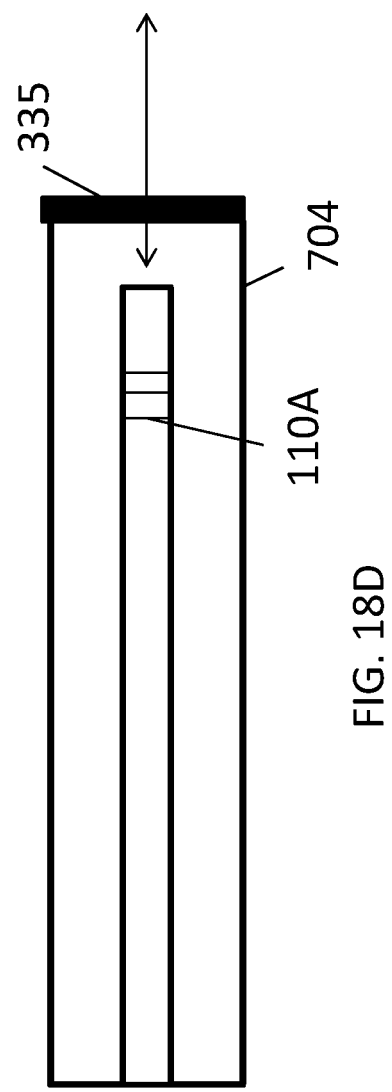
FIG. 18C
FIG. 18D

INTRAVASCULAR FORWARD IMAGING DEVICE

RELATED APPLICATION

This application claims the benefit of and priority to U.S. Provisional Ser. No. 61/745,358, filed Dec. 21, 2012, which is incorporated by reference in its entirety.

FIELD OF THE INVENTION

The present invention generally relates to forward imaging devices for use in medical procedures and methods of using those devices.

BACKGROUND

Cardiovascular disease frequently arises from the accumulation of atheromatous deposits on inner walls of vascular lumen, particularly the arterial lumen of the coronary and other vasculature, resulting in a condition known as atherosclerosis. These deposits can have widely varying properties, with some deposits being relatively soft and others being fibrous and/or calcified. In the latter case, the deposits are frequently referred to as plaque. These deposits can restrict blood flow, which in severe cases can lead to myocardial infarction.

The assessment and treatment of cardiovascular disease often involves imaging the inside of the vessel. This is often performed with an imaging catheter that is inserted into a blood vessel or chamber of the heart in order to diagnose or treat certain conditions. Conventional imaging methods only permit to a large extent the imaging of objects and surfaces located along the sides of catheter. For example, catheters that use piezoelectric transducers for imaging typically employ the transducers at forty-five degree angles to provide conical views.

These limitations of conventional devices can be problematic when it is necessary to image an object directly in front of the catheter rather than along the sides. For example, an artery may be completely blocked with plaque, in what is referred to as a chronic total occlusion. Chronic total occlusions or CTOs are responsible for clinically significant decreases in blood flow. In addition, CTOs often mean more significant intervention, such as coronary artery bypass surgery. Accordingly, the ability to quickly and accurately identify and assess CTOs is vital to the management of cardiovascular disease.

SUMMARY

The invention relates to intraluminal devices having at least one imager configured to image an object in a forward direction. Unlike conventional imaging catheters that can only image objects at oblique angles, the present devices image objects in a forward field of view. The ability to image objects in a forward direction is particularly useful for the assessment and treatment of cardiovascular disease. For example, devices of the invention are able to image the extensive plaque associated with chronic total occlusions; whereas conventional imaging catheters are capable of imaging only plaque accumulated along the walls of an artery.

Any device configured for insertion into the vasculature is useful in connection with the invention. In use, devices of the invention can have a guidewire or catheter configured with an imaging sensor or imager. In fact, both the guidewire and catheter may have imaging sensors. In either of those embodiments, the imaging sensor is able to image an object in a forward direction, providing a perspective that cannot be achieved using conventional devices. From this forward perspective, an operator can better analyze blockages in the vessel. In certain aspects of the invention, the sensor is positioned at the distal tip of the device, which facilitates forward imaging.

In addition to the forward imaging sensor, devices of the invention may also include additional imaging sensors positioned anywhere along the device. The additional imaging sensors provide other perspectives that help provide a more thorough assessment of the vessel interior. The exact number and positioning of the sensors can be adjusted as desired. In certain aspects, these additional imaging sensors are located along the sides of the device for oblique imaging.

Although any sensor is useful for practicing the invention, in certain aspects, the sensor includes an optical fiber. In further aspects of the invention, the optical fiber includes a fiber Bragg grating (FBG), and in particular, a blazed fiber Bragg grating. As encompassed by the invention, light transmitted along the optical fiber hits the blazed FBG, causing light to be emitted at an oblique angle from the device. This emitted light contacts a photoacoustic transducer in the sensor that converts the emitted light to an acoustic signal. When the acoustic signal hits an object, it is reflected back towards the sensor and converted back into an analyzable light signal.

Devices of the invention can further include an image assembly configured to send and receive signals to and from the optical fiber. In certain aspects of the invention, the image receives a signal from the photoacoustic sensor and constructs a visual image based on the signal. In further aspects of the invention, the device may also include a pressure sensor for sensing pressure within the vessel lumen along with imaging the vessel interior.

In addition to the provided devices, the invention also encompasses methods of using such devices. The method can involve providing a forward imaging device comprising an elongated body configured to fit within the lumen of a vessel and at least one imaging sensor located on the elongated body configured to image an object in a forward direction. The method can further involve inserting the device into a lumen of a vessel and imaging an object in a forward direction. The device, as described above, includes an optical sensor configured to image an object in a forward direction. The provided methods are particularly useful in cardiovascular diagnostic procedures when the vessel has been completely blocked by plaque and imaging of the occlusion is required.

BRIEF DESCRIPTION OF THE DRAWINGS

FIGS. 6 and 7 depict an imaging element that uses Fiber Bragg Gratings to generate acoustic energy out of the side of the imaging element.

FIGS. 18A-18D illustrate various catheter embodiments of using optical-acoustic imaging elements for forward imaging.

DETAILED DESCRIPTION

Figure 1:
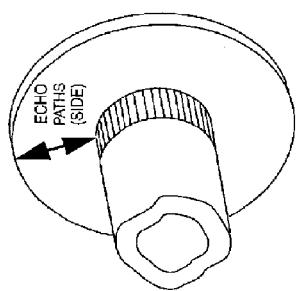
FIG. 1-3 are isometric views showing different imaging planes generated by an ultrasonic catheter tip.

The invention generally relates to forward imaging devices for imaging the inside of a vessel and methods of using such devices. More specifically, the invention relates to devices that include an elongated body configured for insertion into a lumen of a vessel and at least one imaging sensor located on the elongated body configured to image an object in device forward direction. The ability to image an object directly in front of the device provides a unique advantage over conventional imaging catheters that can only image in oblique direction, especially when medical procedures are involved.

Although devices of the present invention are suitable for use with any elongated body, in certain embodiments, the invention encompasses a forward imaging catheter or guidewire. The imaging catheter or guidewire is configured for intraluminal introduction into a target body lumen. The dimensions and other physical characteristics of the catheter or guidewire may vary depending on the body lumen that is to be accessed. In addition, the dimensions can depend on the placement and amount of imaging elements included on the imaging catheter or guidewire.

In certain aspects, the imaging catheter may also serve as a delivery catheter for delivery of some type of a therapeutic device, such as a stent, ablator, or balloon. During the procedure, the imaging catheter may be used to identify the appropriate location and the delivery catheter used to deliver the device to the appropriate location.

For embodiments encompassing a forward looking guidewire, the imaging element can be formed as or be integrated into the body of the imaging guidewire, circumscribe the guidewire, and/or run along the body of the guidewire. The imaging guidewire may also include an outer support structure or coating surrounding the imaging elements. The imaging guidewire including the imaging element (for example, an optical fiber and transducer material) and, in certain embodiments, the surrounding support structure can have a total outside diameter of less than 1 mm, preferably less than 300 micron (less than about 1 French).

The provided forward imaging guidewire bodies may include a solid metal or polymer core. Suitable polymers include polyvinylchloride, polyurethanes, polyesters, polytetrafluoroethylenes (PTFE), silicone rubbers, natural rubbers, and the like. Preferably, at least a portion of the metal or polymer core and other elements that form the imaging guidewire body are flexible.

In certain embodiments, a forward imaging catheter is provided. The imaging element can form or be integrated within the body of the catheter, circumscribe the catheter, placed on a distal end face of the catheter, and/or run along the body of the catheter. The imaging catheter may also include an outer support structure or coating surrounding the imaging elements. Imaging catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French.

Catheter bodies will typically be composed of an organic polymer that is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques. Preferably, at least a portion of the catheter body is flexible.

Figure 2:
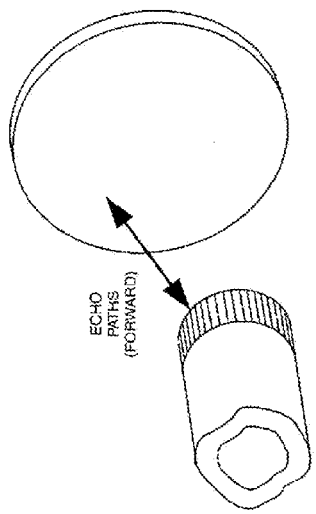
Figure 3:
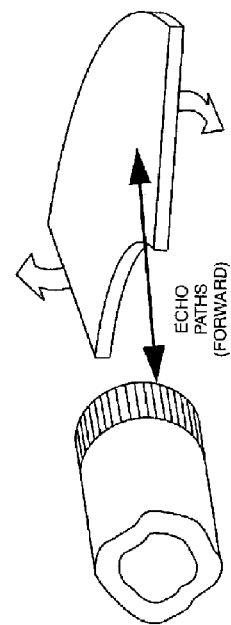

Some of the ultrasonic imaging catheters currently in use are "oblique" or "side viewing" devices which produce B-mode images in a plane which is perpendicular to the longitudinal axis of the catheter and passes through the transducer. That plane can be referred to as the B-mode lateral plane and is illustrated in FIG. 1. There are also "forward viewing" devices that produce a C-mode image plane as illustrated in FIG. 2 which is perpendicular to the axis of the catheter and spaced in front of the transducer. Other forward viewing devices produce a B-mode image in a plane that extends in a forward direction from the transducer and parallel to the axis of the catheter. That plane is referred to as the B-mode forward plane and is illustrated in FIG. 3. The forward viewing devices are particularly advantageous in that they allow the physician to see what is in front of the catheter, and they also allow imaging in areas which cannot be crossed with the catheter. These conventional imaging catheters typically rely on electro-mechanical piezoelectric transducers and associated circuitry to send an electrical signal up and down the device. The electrical signal causes the piezoelectric transducer to emit sound waves from the device, which are then used to image an object as they are reflected from an object surface.

In contrast to these conventional devices, devices of the present invention are optic-based and use optical fibers to transmit optical/light signals along the length of the device. The light signals are used to generate sound waves in the manner explained below, which are then used to image an object as they are reflected from an object surface.

The forward imaging guidewire or catheter of the invention may include an imaging assembly. Any imaging assembly may be used with devices and methods of the invention, such as optical-acoustic imaging apparatus, intravascular ultrasound (IVUS) or optical coherence tomography (OCT). The imaging assembly is used to send and receive signals to and from the imaging surface that form the imaging data.

In preferred embodiments, the imaging assembly is configured to send and receive an optical/light signal through an imaging element of the device. In certain embodiments of the invention, the imaging element comprises an optical fiber through which the imaging assembly sends and receives optical signals. In certain embodiments, the optical fiber includes a Fiber Bragg Grating within the optical fiber. Further detail regarding the imaging elements is provided throughout the present disclosure.

Fiber Bragg Gratings (FBGs) provide a means for measuring the interference between two paths taken by an optical beam. A partially-reflecting Fiber Bragg Grating is used to split the incident beam of light into two parts, in which one part of the beam travels along a path that is kept constant (constant path) and another part travels a path for detecting a change (change path). The paths are then combined to detect any interference in the beam. If the paths are identical, then the two paths combine to form the original beam. If the paths are different, then the two parts will add or subtract from each other and form an interference. The Fiber Bragg Grating elements are thus able to sense a change wavelength between the constant path and the change path based on received ultrasound or acoustic energy. The detected optical signal interferences can be used to generate an image using any conventional means.

In certain embodiments, the imaging element includes a piezoelectric element to generate the acoustic or ultrasound energy. In such aspect, the optical fiber of the imaging element may by coated by the piezoelectric element. The piezoelectric element may include any suitable piezoelectric or piezoceramic material. In one embodiment, the piezoelectric element is a poled polyvinylidene fluoride or polyvinylidene difluoride material. The piezoelectric element can be connected to one or more electrodes that are connected to a generator that transmits pulses of electricity to the electrodes. The electric pulses cause mechanical oscillations in the piezoelectric element, which generates an acoustic signal. Thus, the piezoelectric element is an electric-to-acoustic transducer. Primary and reflected pulses (i.e. reflected from the imaging medium) are received by the Bragg Grating element and transmitted to an electronic instrument to generate an image.

Figure 4:
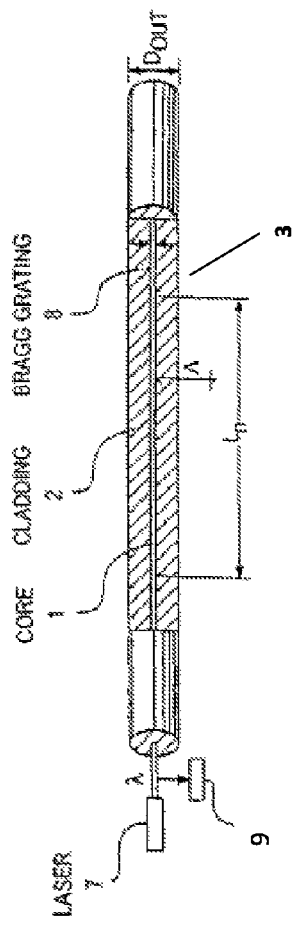
FIG. 4 depicts an optical fiber suitable for use with the provided forward imaging devices.
Figure 5:
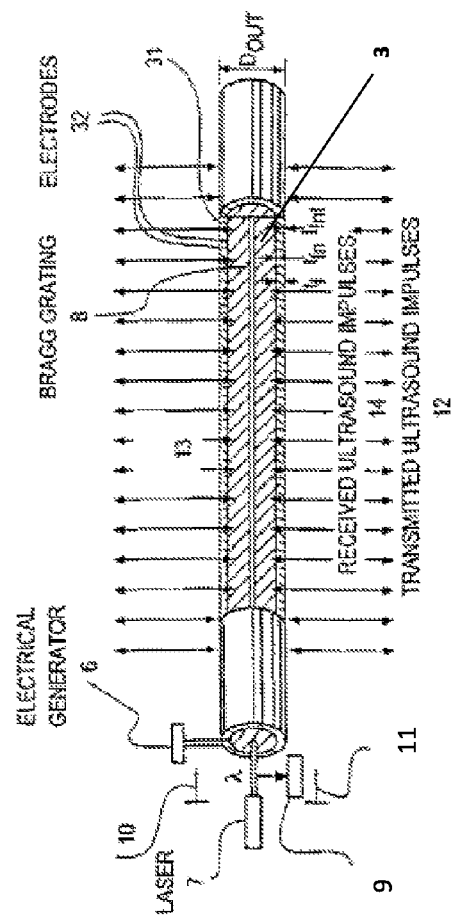
FIG. 5 depicts an embodiment of an imaging element that includes a piezoelectric element.

FIG. 5 depicts an embodiment of an imaging element that includes a piezoelectric element. The imaging element includes an optical fiber 3 (such as the optical fiber in FIG. 4) with Fiber Bragg Grating 8 and a piezoelectric element 31. As shown in FIG. 5, an electrical generator 6 stimulates the piezoelectric element 31 (electrical-to-acoustic transducer) to transmit ultrasound impulses 10 to both the Fiber Bragg Grating 8 and the outer medium 13 in which the device is located. For example, the outer medium may include blood when imaging a vessel. Primary and reflected impulses 11 are received by the Fiber Bragg Grating 8 (acting as an acoustic-to-optical transducer). The mechanical impulses deform the Bragg Grating and cause the Fiber Bragg Grating to modulate the light reflected within the optical fiber, which generates an interference signal. The interference signal is recorded by electronic detection instrument 9, using conventional methods. The electronic instrument may include a photodetector and an oscilloscope. Imaging information regarding the contact between the forward imaging device and the object can be generated from these recorded signals. The electronic instruments 9 modulation of light reflected backwards from the optical fiber due to mechanical deformations. The optical fiber with a Bragg Grating described herein and shown in FIGS. 4-5 and other varying embodiments are described in more detail in U.S. Pat. Nos. 6,659,957 and 7,527,594 and in U.S. Patent Publication No. 2008/0119739.

FIG. 18A illustrates an embodiment of the present invention that utilizes a Fiber Bragg Grating 8 and piezoelectric element 31 to generate and receive imaging signals in front of the catheter. As shown, the optical fiber 3 is curved such that the curved portion is facing a distal end of a catheter body 700. Mechanical impulses from the piezoelectric element at a distal end of the catheter 700 creates an inference signal that is received by the optical fiber 3, which provides imaging data of tissue located in front of the catheter body. FIG. 18B depicts an alternative embodiment of the present invention that utilizes Fiber Bragg Grating 8 and piezoelectric element 31 that does not require bending the optical fiber 3.

In another aspect, the imaging element does not require an electrical-to-acoustic transducer to generate acoustic/ultrasound signals. Instead, the imaging element utilizes the one or more Fiber Bragg Grating elements of the optical fiber in combination with an optical-to-acoustic transducer material to generate acoustic energy from optical energy. In this aspect, the acoustic-to-optical transducer (signal receiver) also acts as an optical-to-acoustic transducer (signal generator).

To generate the acoustic energy, imaging element may include a combination of blazed and unblazed Fiber Bragg Gratings. Unblazed Bragg Gratings typically include impressed index changes that are substantially perpendicular to the longitudinal axis of the fiber core of the optical fiber. Unblazed Bragg Gratings reflect optical energy of a specific wavelength along the longitudinal of the optical fiber. Blazed Bragg Gratings typically include obliquely impressed index changes that are at a non-perpendicular angle to the longitudinal axis of the optical fiber. Blazed Bragg Gratings reflect optical energy away from the longitudinal axis of the optical fiber. FIGS. 6 and 7 depict an imaging element according to this embodiment.

FIG. 6 shows an example of an imaging element that uses Fiber Bragg Gratings to generate acoustic energy. As depicted in FIG. 7, the imaging element 100 includes an optical fiber 105 with unblazed Fiber Bragg Grating 110A and 110B and blazed Fiber Bragg Grating 330 and a photoacoustic material 335 (optical-to-acoustic transducer). The region between the unblazed Fiber Bragg Grating 110A and 110B is known as the strain sensing region 140. The strain sensing region may be, for example, 1 mm in length. The Blazed Fiber Bragg Grating 330 is implemented in the strain sensing region 140. The photoacoustic material 335 is positioned to receive the reflected optical energy from the blazed Fiber Bragg Grating 330. Although not shown, the proximal end of the optical fiber 105 is operably coupled to a laser and one or more electronic detection elements.

In operation and as depicted in FIG. 7, the blazed Fiber Bragg Grating 330 receives optical energy of a specific wavelength λ1 from a light source, e.g. a laser, and blazed Grating 330 directs that optical energy towards photoacoustic material 335. The received optical energy in the photoacoustic material 335 is converted into heat, which causes the material 335 to expand. Pulses of optical energy sent to the photoacoustic material 335 cause the photoacoustic material 335 to oscillate. The photoacoustic material 335 oscillates, due to the received optical energy, at a pace sufficient to generate an acoustic or ultrasound wave. The acoustic wave is transmitted out to and reflected from the object surface back to the imaging element, particularly when the device contacts an object. The acoustic wave reflected from the object surface impinges on photoacoustic transducer 335, which causes a vibration or deformation of photoacoustic transducer 335. This results in a change in length of light path within the strain sensing region 140. Light received by blazed fiber Bragg grating from photoacoustic transducer 135 and into fiber core 115 combines with light that is reflected by either fiber Bragg grating 110A or 110B (either or both may be including in various embodiments). The light from photoacoustic transducer 135 will interfere with light reflected by either fiber Bragg grating 110A or 110B and the light returning to the control unit will exhibit an interference pattern. This interference pattern encodes the image captured by imaging element 100. The light 137 can be received into photodiodes within a control unit and the interference pattern thus converted into an analog electric signal. This signal can then be digitized using known digital acquisition technologies and processed, stored, or displayed as an image of the target treatment site.

FIGS. 18C and 18D illustrate embodiments that utilize the concepts disclosed in reference to FIGS. 6 and 7 with respect to forward imaging. As shown in FIG. 18C, the optical fiber 3 includes a unblazed Fiber Bragg Gratings 110A and 110B and a blazed Fiber Bragg Grating 330 at a curved portion of the optical fiber 3 facing the distal end. The blazed Fiber Bragg Grating 330 transmits optical energy towards the photoacoustic material 335 located at a distal end of the catheter 702. The photoacoustic material oscillates, due to the received optical energy, to generate an acoustic signal. The acoustic signal is transmitted to and reflected back from an object in front of the catheter, which is then sent back to the blazed Fiber Bragg Gratting 330. The received signal can be used to form image data as described above in reference to FIG. 7. The imaging element depicted in FIG. 18D operates in a similar manner but does not require a blazed Fiber Bragg Grating 330. Instead an unblazed Fiber Bragg Grating 110A is used to send the optical signal to the photoacoustic material 335 at the distal end of catheter 704. The unblazed Fiber Bragg Grating 110A also receives the reflected acoustic signal from an object in front of the catheter 704. The received reflected signal can be used to form image data.

Acoustic energy of a specific frequency may be generated by optically irradiating the photoacoustic material 335 at a pulse rate equal to the desired acoustic frequency. The photoacoustic material 335 can be any suitable material for converting optical energy to acoustic energy and any suitable thickness to achieve a desired frequency. The photoacoustic material 335 may have a coating or be of a material that receives acoustic energy over a band of frequencies to improve the generation of acoustic energy by the photoacoustic material and reception of the acoustic energy by the optical fiber imaging region.

In one example, the photoacoustic material 335 has a thickness 340 (in the direction in which optical energy is received from blazed Bragg grating 330) that is selected to increase the efficiency of emission of acoustic energy. In one example, thickness 340 is selected to be about ¼ the acoustic wavelength of the material at the desired acoustic transmission/reception frequency. This improves the generation of acoustic energy by the photoacoustic material.

In a further example, the photoacoustic material is of a thickness 300 that is about ¼ the acoustic wavelength of the material at the desired acoustic transmission/reception frequency, and the corresponding glass-based optical fiber imaging region resonant thickness 300 is about ½ the acoustic wavelength of that material at the desired acoustic transmission/reception frequency. This further improves the generation of acoustic energy by the photoacoustic material and reception of the acoustic energy by the optical fiber imaging region. A suitable photoacoustic material is pigmented polydimethylsiloxane (PDMS), such as a mixture of PDMS, carbon black, and toluene.

The imaging element described and depicted in FIGS. 6 and 7 and other varying embodiments are described in more detail in U.S. Pat. Nos. 7,245,789, 7,447,388, 7,660,492, 8,059,923 and in U.S. Patent Publication Nos. 2010/0087732 and 2012/0108943.

In certain embodiments, an optical fiber of a imaging element (such as one shown in FIGS. 5-7) can include a plurality of Fiber Bragg Gratings, each with its own unique period (e.g., 0.5μ), that interact with at least one other transducer. Because each Fiber Bragg Grating can be directed to transmit and receive signals of specific wavelengths, the plurality of Fiber Bragg Gratings in combination with a tunable filter can be used to generate an array of distributed sonars.

Additional components may be used in conjunction with the forward imaging guidewire or catheter to allow an operator to image an object or surface. These additional components are referred to generally as an imaging assembly.

Figure 8:
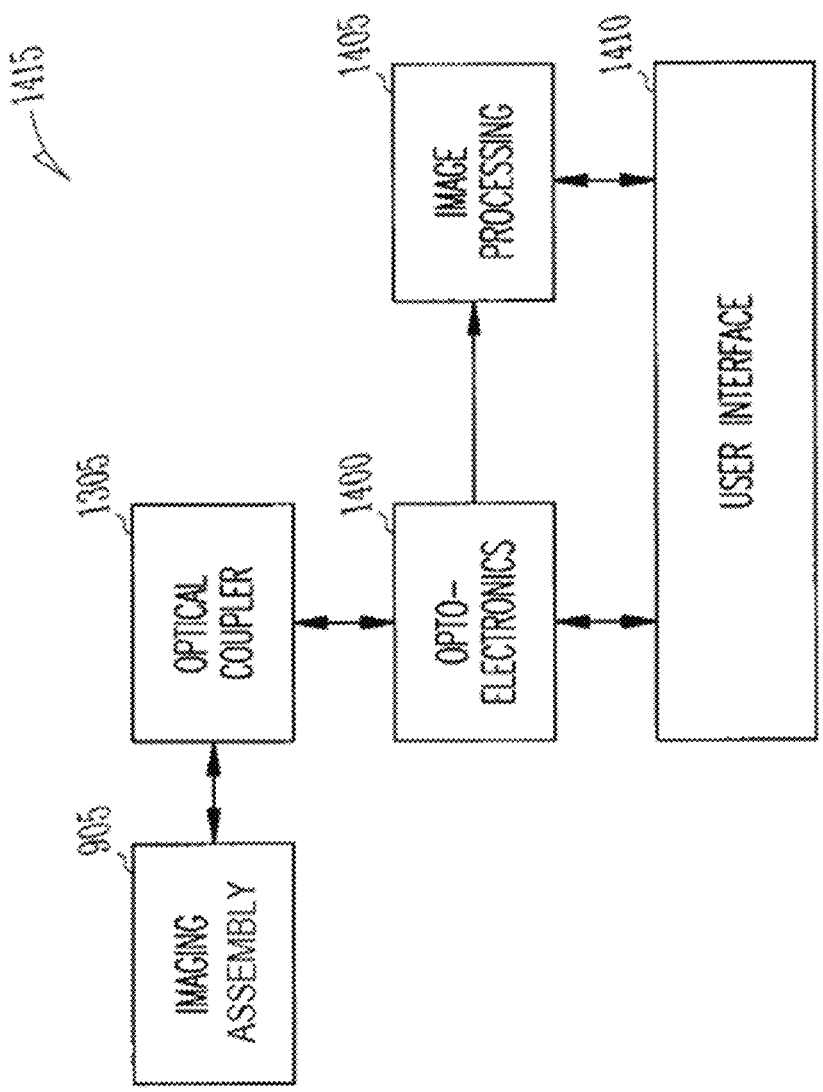
FIG. 8 is a block diagram generally illustrating an image assembly of the invention and several associated interface components.

FIG. 8 is a block diagram illustrating generally an image assembly 905 and several associated interface components. The block diagram of FIG. 8 includes the image assembly 905 that is coupled by optical coupler 1305 to an optoelectronics module 1400. The optoelectronics module 1400 is coupled to an image processing module 1405 and a user interface 1410 that includes a display providing a viewable still and/or video image of the imaging region near one or more acoustic-to-optical transducers using the acoustically-modulated optical signal received therefrom. In one example, the system 1415 illustrated in the block diagram of FIG. 26 uses an image processing module 1405 and a user interface 1410 that are substantially similar to existing acoustic imaging systems.

Figure 9:
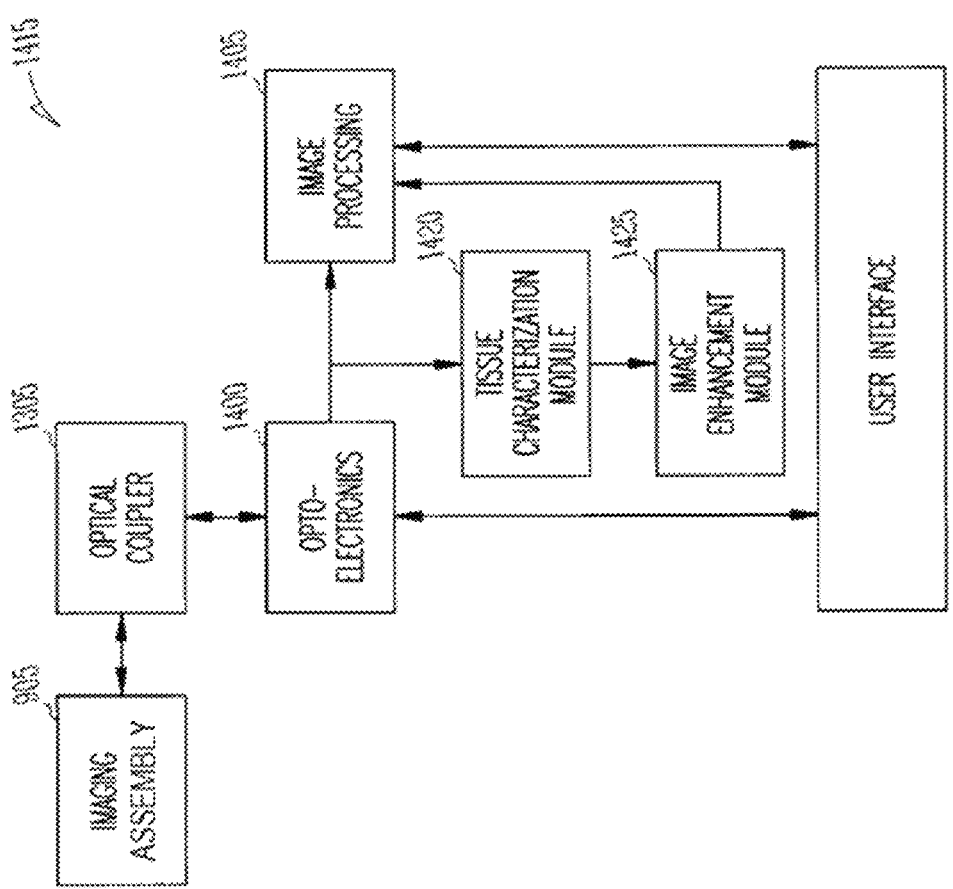
FIG. 9 is a block diagram illustrating another example of an imaging assembly of the invention and associated interface components.

FIG. 9 is a block diagram illustrating generally another example of the image assembly 905 and associated interface components. In this example, the associated interface components include a tissue (and plaque) characterization module 1420 and an image enhancement module 1425. In this example, an input of tissue characterization module 1420 is coupled to an output from optoelectronics module 1400. An output of tissue characterization module 1420 is coupled to at least one of user interface 1410 or an input of image enhancement module 1425. An output of image enhancement module 1425 is coupled to user interface 1410, such as through image processing module 1405.

In this example, tissue characterization module 1420 processes a signal output from optoelectronics module 1400. In one example, such signal processing assists in distinguishing plaque from nearby vascular tissue. Such plaque can be conceptualized as including, among other things, cholesterol, thrombus, and loose connective tissue that build up within a blood vessel wall. Calcified plaque typically reflects ultrasound better than the nearby vascular tissue, which results in high amplitude echoes. Soft plaques, on the other hand, produce weaker and more texturally homogeneous echoes. These and other differences distinguishing between plaque deposits and nearby vascular tissue are detected using tissue characterization signal processing techniques.

For example, such tissue characterization signal processing may include performing a spectral analysis that examines the energy of the returned ultrasound signal at various frequencies. A plaque deposit will typically have a different spectral signature than nearby vascular tissue without such plaque, allowing discrimination therebetween. Such signal processing may additionally or alternatively include statistical processing (e.g., averaging, filtering, or the like) of the returned ultrasound signal in the time domain. Other signal processing techniques known in the art of tissue characterization may also be applied. In one example, the spatial distribution of the processed returned ultrasound signal is provided to image enhancement module 1425, which provides resulting image enhancement information to image processing module 1405. In this manner, image enhancement module 1425 provides information to user interface 1410 that results in a displaying plaque deposits in a visually different manner (e.g., by assigning plaque deposits a discernible color on the image) than other portions of the image. Other image enhancement techniques known in the art of imaging may also be applied. In a further example, similar techniques are used for discriminating between vulnerable plaque and other plaque, and enhancing the displayed image provides a visual indicator assisting the user in discriminating between vulnerable and other plaque.

The opto-electronics module 1400 may include one or more lasers and fiber optic elements. In one example, such as where different transmit and receive wavelengths are used, a first laser is used for providing light to the imaging assembly 905 for the transmitted ultrasound, and a separate second laser is used for providing light to the imaging assembly 905 for being modulated by the received ultrasound. In this example, a fiber optic multiplexer couples each channel (associated with a particular one of the optical fibers 925) to transmit and receive lasers and associated optics. This reduces system complexity and costs.

In one example, the sharing of transmission and reception components by multiple guidewire channels is possible at least in part because the acoustic image is acquired over a relatively short distance (e.g., millimeters). The speed of ultrasound in a human or animal body is slow enough to allow for a large number of transmit/receive cycles to be performed during the time period of one image frame. For example, at an image depth (range) of about 2 cm, it will take ultrasonic energy approximately 26 microseconds to travel from the sensor to the range limit, and back. In one such example, therefore, an about 30 microseconds transmit/receive (T/R) cycle is used. In the approximately 30 milliseconds allotted to a single image frame, up to 1,000 T/R cycles can be carried out. In one example, such a large number of T/R cycles per frame allows the system to operate as a phased array even though each sensor is accessed in sequence. Such sequential access of the photoacoustic sensors in the guidewire permits (but does not require) the use of one set of T/R opto-electronics in conjunction with a sequentially operated optical multiplexer.

In certain aspects, one or more imaging elements are incorporated into a forward imaging guidewire. The provided forward imaging guidewire allows one image a luminal surface prior to introducing a catheter into a body lumen, e.g., a blood vessel. Because the imaging guidewire obtains images of the luminal surface, an operator can use the imaging guidewire to find a region of interest within the vasculature prior to introducing a catheter device. The one or more imaging elements can be formed around an inner guidewire body, integrated into an inner guidewire body, or form the guidewire body itself. The imaging guidewire may include a support structure covering at least a portion of the imaging element. The support structure can include one or more imaging windows that allow the imaging element to send and receive signals that form the imaging data.

Figure 10:
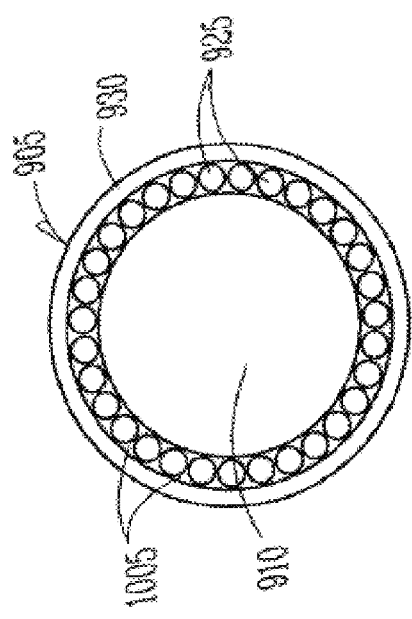
FIG. 10 shows a cross-section of an exemplary forward imaging guidewire, including a plurality of imaging elements.

In one example, a plurality of imaging elements surrounds an inner guidewire body. FIG. 10 shows a cross-section of the imaging guidewire 905 showing a plurality of imaging elements surrounding the inner guidewire body 910. The imaging elements 925 are placed next to each other, parallel to, and along the length of the inner guidewire body 910. The guidewire body 910 can be any suitable flexible material. A binder material 1005 can provide structure support to the imaging elements 925. The imaging elements 925 are optionally overlaid with a protective outer coating 930 that provides for transmission of imaging signals.

Typically, the imaging elements are placed parallel to and along the length of the guidewire. In such aspect, the imaging elements image surfaces substantially perpendicular to the longitudinal axis of the imaging guidewire. However, other configurations may be used. For example, one or more imaging elements may be wrapped around the inner guidewire body. In addition, it is also contemplated at least a portion of the imaging elements are positioned substantially across the longitudinal axis of the guidewire. For example, the imaging elements can be positioned across a distal tip of the imaging guidewire such that the imaging elements image objects or surfaces in front of the imaging guidewire.

Figure 11:
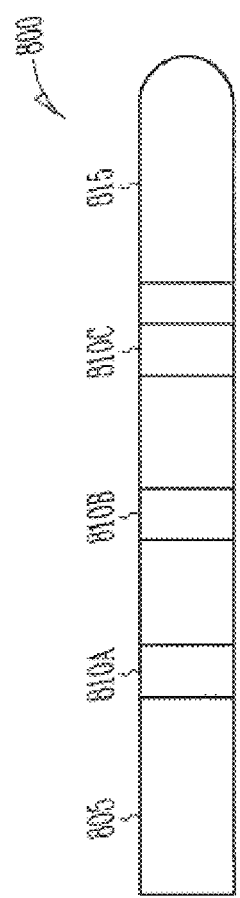
FIG. 11 depicts a distal portion of an exemplary forward imaging guidewire.

In certain embodiments, the imaging guidewire further includes a support structure surrounding the one or more imaging elements. The support structure may include a plurality of windows to allow transmission and reception of signals (e.g. acoustic signals). FIG. 11 depicts a distal portion 800 of an imaging guidewire 805 according to one embodiment. The imaging guidewire 805 includes one or more windows 810A, 810B, . . . , 810N. Each window 810 may expose at least a portion of one or more imaging elements. The exposed portion of each imaging element may include one or more acoustic-to-optical transducers (e.g. Fiber Bragg Grating in an optical fiber) that correspond to one or more optical-to-acoustic transducers (i.e. photoacoustic material) or one or more electrical-to-acoustic transducers (i.e. piezoelectric material).

The imaging guidewire of the invention may be used in conjunction with any type of catheters, including delivery catheters. Furthermore, the provided forward imaging catheters are suitable for use with any type of guidewire.

The forward imaging catheter allows an operator to obtain images of a luminal surface as the catheter is slideably moved along a guidewire to the location of interest. In certain embodiments, the forward imaging catheter is a combination catheter that can perform intraluminal procedures such as delivering implants, ablation, and extraction.

Like the forward imaging guidewire, the forward imaging catheter includes one or more imaging elements. As discussed previously, each imaging element includes an optical fiber that may comprise a Fiber Bragg Grating. Like the forward imaging guidewire, the imaging elements can be positioned anywhere along and on the inner body of the imaging catheter.

Figure 12:
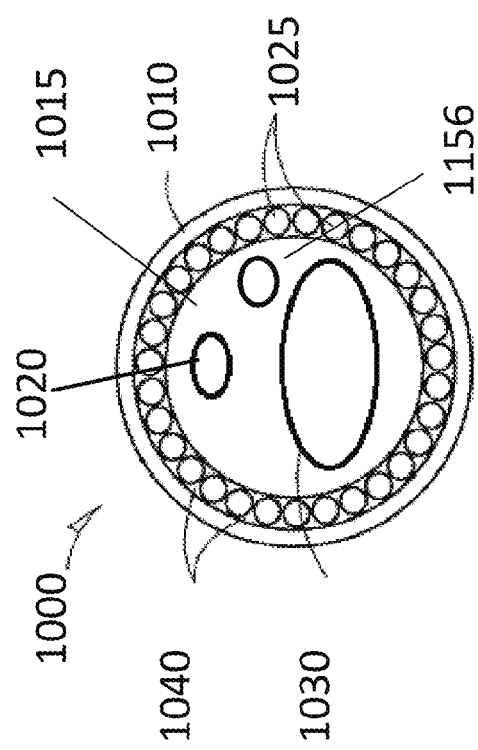
FIG. 12 illustrates a cross-sectional view of an exemplary forward imaging catheter.

For example, FIG. 12 illustrates a cross-sectional view of a forward imaging catheter 1000 according to one embodiment. The forward imaging catheter 1000 includes imaging elements 1025 that surround an inner body member 1015 of the forward imaging catheter 1000. The imaging elements 1025 are positioned next to each other, parallel to, and along the length of the inner body member 1015. As shown in the cross-sectional view, the imaging elements 1025 are arranged around the circumference of the inner body member 1015 of the forward imaging catheter 1000. The imaging elements 1025 are disposed in binding material 1040. The imaging elements 1025 may, for example, include transducers positioned to allow imaging in a forward direction. For example, rather than being positioned so that sound is emitted obliquely to the axis of the catheter, the transducers can be positioned right at the tip to face outward, in the same direction that the catheter is facing. The imaging element may also include a plurality of transducers along the optical fiber, such that some are positioned along the sides of the catheter, for oblique imaging, and other transducers are positioned at the tip to emit in the direction that the catheter tip is facing. The forward imaging catheter 1000 may be surrounded by an outer catheter sheath or protective coating 1010. The outer catheter sheath or protective coating 1010 can be made from any acoustically transparent resiliently flexible material such as polyethylene or the like, which will permit such transparency while maintaining a sterile barrier around the imaging elements.

Further shown in FIG. 12, the forward imaging catheter 1000 includes a guidewire lumen 1020. The guidewire lumen 1020 receives at least a portion of a guidewire. The forward imaging catheter 1000 can be designed as an over-the-wire catheter or a rapid exchange catheter. Over-the-wire catheters include a guidewire lumen that runs the full length of the catheter. Rapid exchange catheters include a guidewire lumen extending only through a distal portion of the catheter. With respect to the remaining proximal portion of the catheter, the guidewire exits the internal catheter lumen through a guidewire exit port, and the guidewire extends in parallel along the proximal catheter portion.

The forward imaging catheter 1000 may optionally, and as shown in FIG. 12, include one or more tool lumens 1030. The tool lumen 1030 is formed from an inner catheter sheath or member that is disposed within the inner body 1015 of the forward imaging catheter 1000. Through the tool lumen 1030, a catheter tool or device can be introduced into a body lumen, such as blood vessel, for treatment. In addition, the forward imaging catheter may optionally include a removal lumen 1056 that extends from the distal end of the imaging catheter to an opening operably associated with a vacuum source. During intraluminal procedures, a tool element may shave off plaque or other substances from the vessel wall that needs to be removed from the lumen. The shaved-off plaque can be removed from the removal lumen.

Figure 13:
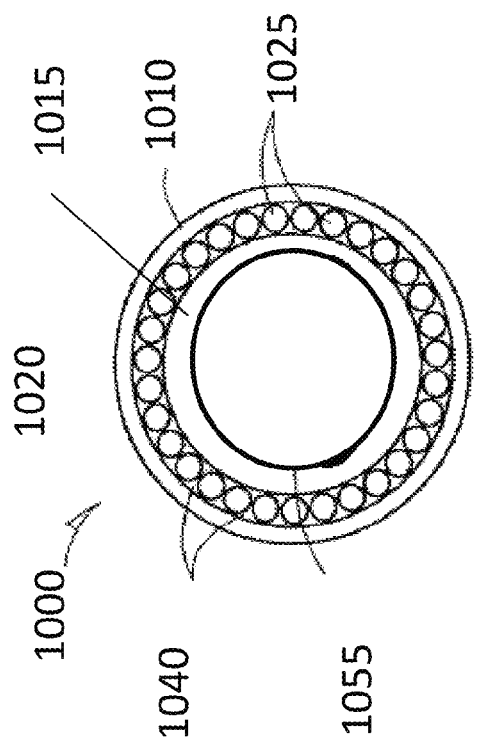
FIG. 13 depicts another exemplary embodiment of an imaging catheter.

FIG. 13 depicts another embodiment of the forward imaging catheter 1000. In this embodiment, the imaging catheter includes a combined lumen 1055 for receiving the catheter tool or device and the imaging guidewire. The combined lumen 1055 is helpful when the catheter tool or device must also circumscribe the guidewire. For example, implants placed within a body vessel and implant delivery mechanisms are often driven over the guidewire so that the implant may be placed flush against the vessel without the guidewire obstructing implant placement.

In addition to the aforementioned imaging sensors, devices of the invention can include a pressure sensor (e.g. a crystalline semi-conductor sensor) for measuring pressure. In certain embodiments, the pressure sensor is located on a distal portion of the device.

A pressure sensor allows one to obtain pressure measurements within a body lumen. A particular benefit of pressure sensors is that pressure sensors allow one to measure of fractional flow reserve (FFR) in vessel, which is a comparison of the pressure within a vessel at positions prior to the stenosis and after the stenosis. The level of FFR determines the significance of the stenosis, which allows physicians to more accurately identify hemodynamically relevant stenosis. For example, an FFR measurement above 0.80 indicates normal coronary blood flow and a non-significant stenosis. Another benefit is that a physician can measure the pressure before and after an intraluminal intervention procedure to determine the impact of the procedure.

A pressure sensor can be mounted on the distal portion of a flexible elongate member. In certain embodiments, the pressure sensor is positioned distal to the compressible and bendable coil segment of the elongate member. This allows the pressure sensor to move away from the longitudinal axis and coil segment as bended. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires can be connected to opposite ends of the resistor and extend within the flexible elongate member to the proximal portion of the flexible elongate member. Additional details of suitable pressure sensors that may be used with devices of the invention are described in U.S. Pat. No. 6,106,476. U.S. Pat. No. 6,106,476 also describes suitable methods for mounting the pressure sensor 104 within a sensor housing.

Figure 14:
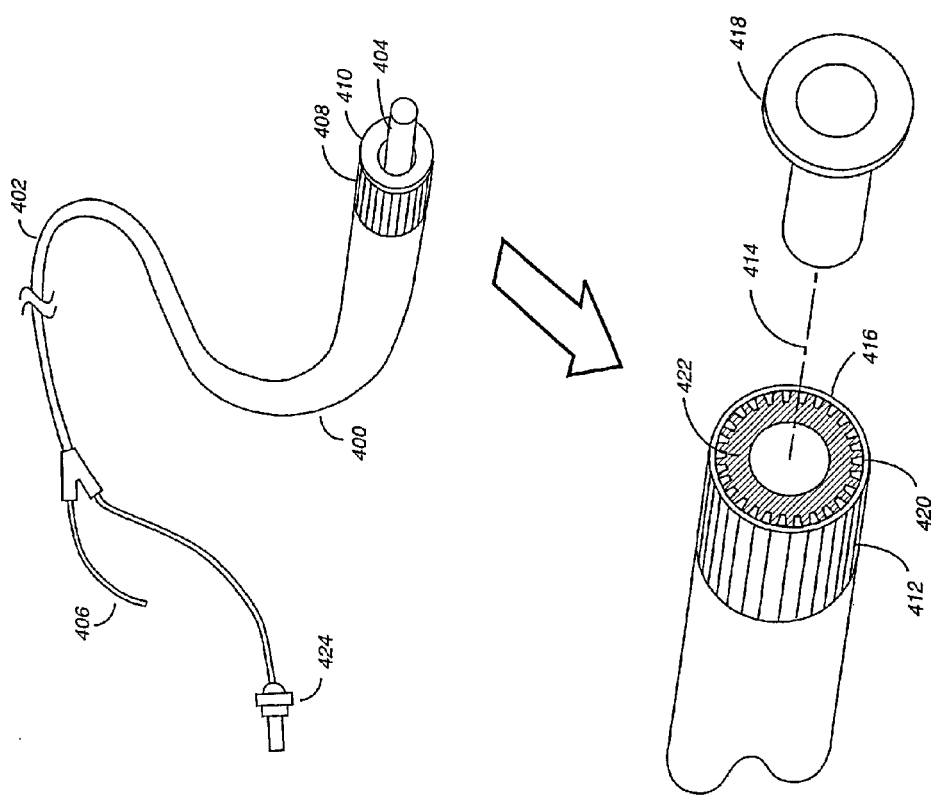
FIG. 14 is a drawing of one embodiment an ultrasonic imaging catheter with a guide wire and central distal lumen utilizing a ultrasonic transducer array assembly according to the present invention.

Reference will now be made to FIG. 14, which depicts an exemplary forward imaging catheter that incorporates the imaging elements described above. It is to be understood that that the present invention is not limited to the embodiments depicted in the provided figures and that other configurations are encompassed. Referring now to FIG. 14, there is shown a catheter 400 for intravascular use. This catheter has an elongated flexible body 402 with an axially extending lumen 404 through which a guide wire 406, fluids, and/or various therapeutic devices or other instruments can be passed. The invention is not, however, limited to use with a catheter, and it can be utilized with any suitable catheter, guide wire, probe, etc. An ultrasonic imaging transducer assembly 408 is provided at the distal end 410 of the catheter, with a connector 424 located at the proximal end of the catheter. This transducer 408 comprises a plurality of imaging elements 412 that are preferably arranged in a cylindrical array centered about the longitudinal axis 414 of the catheter for transmitting and receiving ultrasonic energy. As explained above, the imaging elements or sensors of the invention comprise an optical fiber and in certain embodiments, the optical fibers comprise fiber Bragg gratings and piezoelectric transducers to emit and/or receive ultrasonic energy.

The imaging elements 412 are mounted on the inner wall of a cylindrical substrate 416 which, in the embodiment illustrated, consists of a flexible material that has been rolled into the form of a tube. The end portions 420 of the imaging elements 412 are shown at the distal portion of the transducer assembly. A transducer backing material 422 with the proper acoustical properties surrounds the imaging elements 412. An end cap 418, which isolates the ends of the transducer elements, is attached to the transducer assembly. Alternatively, the end portions 420 of the transducer elements 412 can be covered with nonconductive adhesive in order to insulate them from external fluids (e.g., blood).

As explained previously, the imaging elements can comprise, in certain embodiments, piezoelectric transducers. A piezoelectric transducer, when properly excited, will perform a translation of electrical energy to mechanical energy, and as well, mechanical to electrical. The effectiveness of these translations depends largely on the fundamental transduction efficiency of the transducer assembly taken as a whole. The transducer is a three dimensional electro-mechanical device though, and as such is always capable of some degree of electro-mechanical coupling in all possible resonate modes, with one or several modes dominating. Generally an imaging transducer design seeks to create a single dominate mode of electro-mechanical coupling, suppressing all other coupling modes as "spurious." The common method used to accomplish a transducer design with a single dominate mode of electro-mechanical coupling usually rests in the creation of a single, efficient mechanical coupling "port" to the medium outside of the transducer. The single port is created by mounting the transducer such that the most efficient resonant mode of transducer operation faces that mechanical coupling port, with all other modes suppressed by means of mechanical dispersion attained by transducer dimensional control and dampening materials.

In the design of the present invention, the transducer design utilizes the fact that a transducer can be effective in two principal coupling modes, each mode using a different frequency of operation, acoustic "port", and electro-mechanical coupling efficiency. One port is the "side looking" port that is used in the cross-sectional view image as shown in FIG. 1. The other port is the "end", or, "forward looking" port of the array.

The present invention allows the two coupling modes (i.e. "side" and "forward") to be always active, without any mechanical switching necessary to choose one mode exclusive of the other. The design of this invention also assures that echoes of any image target in the "side looking" plane (see FIG. 1) do not interfere with the target reconstruction in the "forward looking" planes (see FIGS. 2 and 3), and reciprocally, image targets from the "forward looking" do not interfere with the target reconstruction in the "side looking" planes. In accordance with the invention, the design methods listed below are used to maintain sufficient isolation between the two modes of operation. Although as described below, the transducer is an ultrasound transducer, it is understand that the optical acoustic transducer, described above can be adapted for forward imaging in different coupling modes by using optical energy instead of electrical energy.

A). Resonant and Spatial Isolation of the Two Modes

The "side looking" port is designed for approximately twice the frequency of the "forward looking" port in accordance with the preferred embodiment. The transducer dimensional design is such that the "high frequency and side looking" transducer port sensitivity to low frequency signals, and as well the "low frequency and forward looking" transducer port to high frequency signals, is very low.

Additionally, the transmit and receive acoustic "beam" directions of the two modes are at approximately right angles to each other and this feature offers an additional isolation with respect to image target identification. Also, as a means to further promote isolation between the two modes of operation, and as well optimize a sparse array echo collection method, the echo collection process in "forward" beam reconstruction uses an intentional physical separation of transmitting and receiving imaging elements of preferably 10 elements or more in the circular array annulus. This physical separation aids in preventing "spurious" transmit echoes from the "high frequency side looking" port from contaminating the receiving element listening to "forward only" echoes at the its lower frequency of operation.

B). Electrical Frequency Band Isolation of the Two Modes

As stated previously, the two modes of operation are operated at center frequencies that differ by about a factor of two. This design feature allows for additional isolation between the two modes through the use of band pass filters in the host system that is processing the echo signals received from the catheter. Additionally, if one or both of the two modes is operated in a low fractional bandwidth design (i.e. <30%), the bandpass filters will be even more effective in the maintenance of very high modal isolation.

C). Beam Formation Isolation Through Synthetic Aperture Reconstruction

Synthetic aperture beam reconstruction is used for all image modes. The beam formation process will preferentially focus only on image targets that are coherently imaged in a particular image plane. Thus, while image reconstruction is forming an image in, for example, the "side looking" plane, targets that may have contaminated the echoes from the "forward looking" planes will be generally incoherent and will be suppressed as a type of background noise. The reciprocal is also true: "side looking" echoes contaminants will be generally incoherent in "forward looking" imaging and will be suppressed through the process of synthetic aperture reconstruction.

A flexible digital image reconstruction system is required for the creation of multiple image planes on demand. The preferred method of assembling multiple image planes utilizes a synthetic aperture reconstruction approach. The "side looking" image shown in FIG. 1 can be reconstructed using sampled imaging element apertures as large as for example 14 contiguous imaging elements in a 64 total imaging element circular array. The transmit-receive echo collection for aperture reconstruction can be continuously shifted around the circular array, sampling all transmit-receive cross-product terms to be used in a particular aperture reconstruction. Within any 14-element aperture there can be 105 independent transmit-receive echo cross products used to construct the image synthetically.

"Forward looking" images shown in FIGS. 2 and 3 can be reconstructed using sampled apertures that consist of selected transducer elements arranged on the annulus end of the circular array. For the 64 imaging element example mentioned above, all elements may contribute to a complete data set capture (this would consist of 64 by 32 independent transmit-receive element cross-products) to form a "forward looking" image in either C-mode or B-mode. As an alternative to the complete data set approach, a reduced number of independent transmit-receive element cross-products are used to adequately formulate the image. The transmit-receive echo collection for aperture reconstruction can be continuously shifted around the circular array, sampling all transmit-receive element cross-products to be used in a particular aperture reconstruction.

Special signal processing may be advantageous, especially in the "forward looking" imaging modes that use a less efficient transducer coupling coefficient (k31) and as well may suffer from additional diffraction loss not experienced in the "side looking" mode of synthetic aperture imaging. In forming a "forward looking" C-mode image plane as an example, a low noise bandwidth can be achieved by using a high number of transmit pulses and a narrow bandpass echo filter in the processing system. Additionally, or as a preferred alternative, a matched filter implementation from the use of correlation processing may be used to improve the echo signal-to-noise ratio.

The advantage of this cross-sectional B-mode operation of the catheter imaging device is in its ability to see an image at great depth in the radial dimension from the catheter, and at high image resolution. This depth of view can help aid the user of the catheter to position the device correctly prior to electronically switching to a "forward viewing" mode of operation. Image targets moving quickly in a path generally parallel to the long axis of the catheter can be detected and displayed as a colored region in this mode; this information can be used to compare and confirm moving target information from the "forward viewing" mode of operation of the catheter to enhance the usefulness of the imaging tool.

1. Transducer Operation

The transducer in this "primary" mode operates in the thickness extensional (TE) resonance, utilizing the k33 electro-mechanical coupling coefficient to describe the coupling efficiency. This "thickness resonance" refers to a quarter wave or half wave (depending on the acoustic impedance of the transducer backing formulation) resonance in the transducer dimension that is in alignment with the polarization direction of the transducer, and also the sensed or applied electric field. This TE mode utilizes a typically high frequency thickness resonance developed in the transducer short dimension following either electric field excitation to generate ultrasound acoustic transmit echoes, or, in reception mode following acoustic excitation to generate an electric field in the transducer.

Array Stepping:

The TE mode is used for generating a cross-sectional B-mode image. This cross-section image cuts through the array elements in an orthogonal plane to the long axis of the transducer elements. Echo information gathered from sequential transducer element sampling around the array allows for the synthetically derived apertures of various sizes around the array. For the creation of any synthetically derived aperture, a contiguous group of transducer elements in the array are sequentially used in a way to fully sample all the echo-independent transmit-receive element pairs from the aperture. This sequencing of elements to fully sample an aperture usually involves the transmission of echo information from one or more contiguous elements in the aperture and the reception of echo information on the same or other elements, proceeding until all the echo independent transmit-receive pairs are collected.

Modal Dispersion:

The TE mode transducer operation will exist with other resonant modes simultaneously. The efficiency of electromechanical energy coupling however for each mode though depends on primarily these factors: a) the k coefficient that describes the energy efficiency of transduction for a given resonance node, b) the acoustic coupling path to the desired insonification medium, and c) the echo transmission-reception signal bandwidth matching to the transducer resonance for that particular mode. Thus, for the creation of a "side looking" image, a transducer design is created to optimize the factors above for only the TE resonance, while the other resonant modes within a transducer are to be ignored through the design which suppresses the undesired resonances by minimizing the energy coupling factors mentioned above.

Through this frequency dispersion of unwanted coupling, the desired echoes transmitted and received from the "side looking" transducer port necessary to create a B-mode image plane will be most efficiently coupled through the TE resonance mode within any particular element. Therefore, the proposed transducer design which features a high efficiency TE mode coupling for desired echoes and frequency dispersion of the unwanted resonances and echoes, along with the other modal isolation reasons stated in an earlier section, constitutes a means for high quality TE echo energy transduction for only those desired in-plane echoes used in the creation of the B-mode cross-sectional image plane.

2. System Operation for the Standard Cross-Sectional B-Mode Imaging

Figure 15:
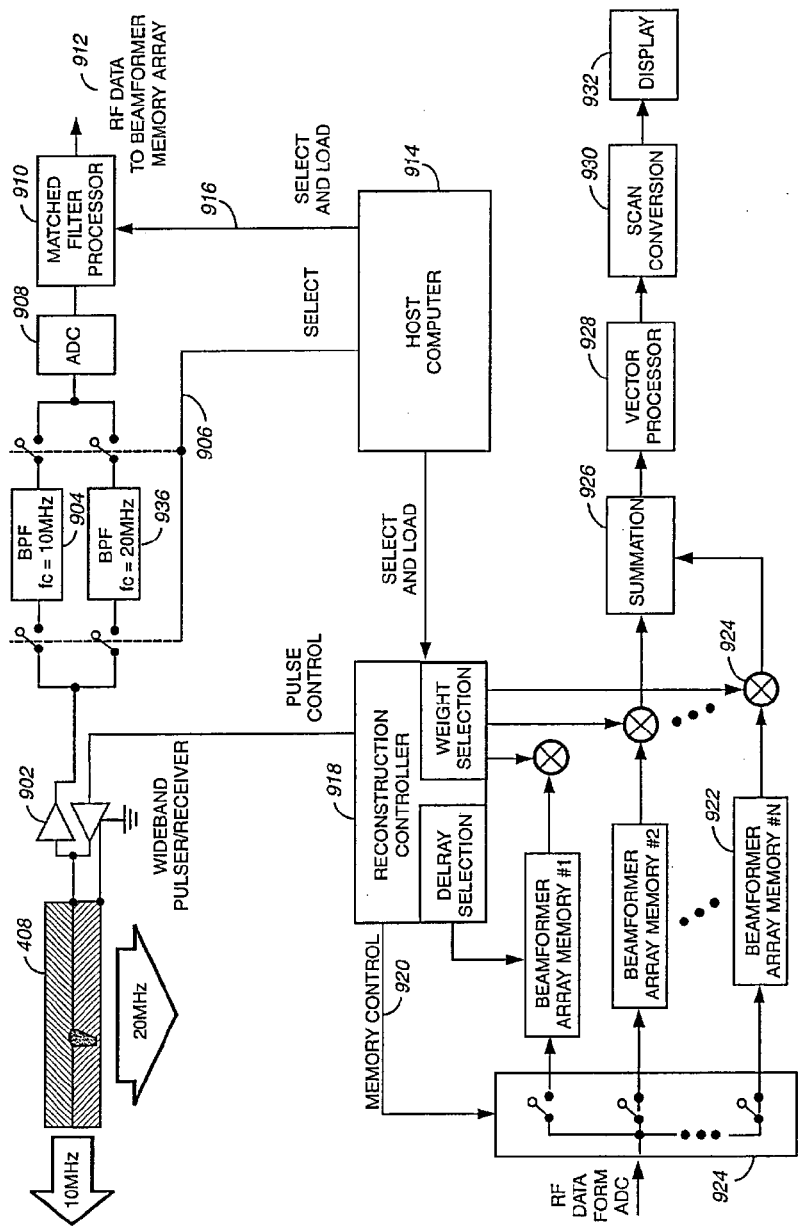
FIG. 15 shows a block diagram of an ultrasound system in accordance with the present invention.

The host ultrasound processing system shown in FIG. 15 controls the ultrasound array 408 element selection and stepping process whereby a single element 412 or multiple elements will transmit and the same or other elements will receive the return echo information. The elements in the array that participate in a given aperture will be sampled sequentially so that all essential cross product transmit-receive terms needed in the beam forming sum are obtained. The host processing system or computer 914 and reconstruction controller 918 will control the transmit pulse timing provided to wideband pulser/receiver 902, the use of any matched filter 910 via control line 916 to perform echo pulse compression. The echo band pass filter (BPF) processing paths in the system are selected using control signal 906 to select between either the 10 MHz 904 or 20 MHz 936 center frequency BPF paths. The amplified and processed analog echo information is digitized using ADC 908 with enough bits to preserve the dynamic range of the echo signals, and passed to the beam-former processing section via signal 912. The beam former section under the control of reconstruction controller 918 uses stored echo data from all the transmit-receive element pairs that exist in an aperture of interest. As the element echo sampling continues sequentially around the circular array, all element group apertures are "reconstructed" using well known synthetic aperture reconstruction techniques to form beam-formed vectors of weighted and summed echo data that radially emanate from the catheter surface using beam-former memory array 922, devices 924 and summation unit 926. Memory control signal 920 controls switch bank 924 which selects which memory array to store the incoming data.

The vector echo data is processed through envelope detection of the echo data and rejection of the RF carrier using vector processor 928. Finally a process of coordinate conversion is done to map the radial vector lines of echo data to raster scan data using scan converter 930 for video display using display 932.

This processing system, through the host control, may also accomplish a blood velocity detection by tracking the blood cells through the elevation length of the transducer beams. The tracking scheme involves a modification of the element echo sampling sequencing and the use of the beamformer section of the host processing system. The blood velocity information may be displayed as a color on the video display; this blood velocity color information is superimposed on the image display to allow the user to see simultaneous anatomical information and blood movement information.

Forward Looking Cross-Sectional C-Mode Operation

The advantage of this "forward looking" operation of the catheter imaging device is in its ability to see an image of objects in front of the catheter where possibly the catheter could not otherwise physically traverse. A "forward" C-mode plane produces a cross-sectional view similar to the standard B-mode cross-sectional view, and so can offer comparable image interpretation for the user, and as well this forward image plane is made more useful because the user can see the presence of image targets at the center of the image, otherwise obscured in the standard cross-sectional view by the catheter itself. This forward view allows also the ideal acoustic beam positioning for the detection and color image display of Doppler echo signals from targets moving generally in parallel with the long axis of the catheter device.

1. Transducer Operation

The transducer in this "secondary" mode operates in the length extensional (LE) resonance, utilizing the k31 electro-mechanical coupling coefficient to describe the coupling efficiency. In this mode of operation, the poling direction of the transducer element and the sensed or applied electric field in the transducer are in alignment, but the acoustic resonance is at 90 degrees to the electric field and poling direction. This "length resonance" refers fundamentally to a half wave resonance in the transducer element's length dimension that is at 90 degrees with the polarization direction of the transducer. The LE mode of resonance, which is typically much lower in resonant frequency than the TE mode because the element length is normally much longer than the thickness dimension, always exists to some extent in a typical transducer array element, but is usually suppressed through a frequency dispersive design.

In some embodiments, the invention utilizes an abrupt physical discontinuity in the transducer element to allow a half wave LE resonance to manifest itself at a desired frequency, in the case of the preferred embodiment, at about one half the frequency of the TE mode resonance. A unique feature of this invention is a mechanically fixed transducer design that allows two resonant modes to operate at reasonably high efficiencies, while the "selection" of a desired mode (i.e. "side", or "forward") is a function of a) an electronically selected frequency band of interest, b) a transducer design that spatially isolates the echo beam patterns between the two modes, and c) image plane specific beam forming weights and delays for a particular desired image plane to reconstruct using synthetic aperture beam-forming techniques, where echo timing incoherence between the "side" and "forward" beam patterns will help maintain modal isolation. Further detail on the use of a notch in transducer assemblies is provided in U.S. Pat. No. 6,780,157, incorporated by reference herein in its entirety.

As discussed earlier, a resonant mode in a transducer design can be made efficient in electro-mechanical energy coupling if at least the three fundamental factors effecting coupling merit are optimized, namely a) the k coefficient (in this case it is the k31 electro-mechanical coupling coefficient) that describes the energy efficiency of transduction for a given resonance node, b) the acoustic coupling path to the desired insonification medium, and c) the echo transmission-reception signal bandwidth matching to the transducer resonance for that particular mode. The invention allows for reasonable optimization of these factors for the LE mode of resonance, although the LE mode coupling efficiency is lower than that of the TE mode coupling. The k31 coupling factor, used in describing LE mode efficiency, is typically one half that of k33, the coupling factor that describes the TE mode efficiency.

The abrupt acoustical discontinuity in the transducer element is created at a step in the assembly of the array. Following the attachment of the transducer material to the flex circuit to create a mechanical bond and electrical connection between the transducer block and the flex circuit, while the transducer material is still in block form, a dicing saw cut can be made the entire length of the transducer material block, creating the notch. The notch depth should be deep enough in the transducer material to create an abrupt discontinuity in the distal portion of the transducer material to allow for a high efficiency LE mode half wave resonance to exist in this end of the transducer element. The saw cut should not be so deep as to sever the ground electrode trace on the transducer block side bonded to the flex circuit. The cut should ideally have a taper on the proximal side to allow for acoustically emitted energy to be reflected up into the backing material area and become absorbed.

It is not desirable that any acoustic coupling exist between the LE modes of resonance in the distal and proximal transducer regions separated by the notch. The distal transducer region LE mode half wave resonance will exist at 10 MHz in PZT (Motorola 3203HD) for a length of about 170 microns between the distal end of the transducer element and the notch. The proximal transducer region LE mode resonance will exist at a frequency considered out of band (approximately 6 MHz) in the two embodiments shown in FIGS. 5 and 7 so as to minimally interfere with the desired operating frequencies (in this case 10 MHz LE mode resonance in the distal region for "forward" acoustic propagation, and 20 MHz TE mode resonance in the entire active field length of the transducer).

The desired acoustic energy coupling port of the distal transducer LE resonant mode region is at the distal end of the catheter array. To protect the end of the array and potentially act as an acoustic matching layer, an end cap made of polyurethane could be used, or alternatively, a uniform coating of adhesive material would suffice. The beam pattern produced by this acoustic port must be broad enough to insonify a large area that covers intended extent of the image plane to be formed. To this end, the beam pattern must typically be at least 60 degrees wide as a "cone shaped" beam measured in the plane to be formed at the half-maximum intensity angles for 2-way (transmitted and received) echoes. The preferred design of the array has 64 or more elements, and a transducer sawing pitch equal to pi times the catheter array diameter divided by the number of elements in the array. For an effective array diameter of 1.13 mm and 64 elements, the pitch is 0.055 mm. Using two consecutive array elements as a "single" effective LE mode acoustic port can provide an adequate, uniform beam pattern that produces the required 60-degree full-width half maximum ("FWHM") figure of merit. The aperture of this "single" forward looking port is then approximately 0.080 mm by 0.085 mm (where 0.085 mm is twice the pitch dimension minus the kerf width of 0.025 mm).

The transducer design may also include a version where no notch is needed in the transducer block. In this case, the driven electrode can exist all along one surface of the transducer element, and the ground or reference electrode can exist all along the opposite side of the element. The long axis length of the transducer will resonate at a half wavelength in LE mode, and the thickness dimension will allow the production of a TE mode resonance in that thickness dimension. In order for this design to operate though, the LE and TE mode resonant frequencies will be quite different in order to maintain the proper TE mode elevation beam focus. As an example, in maintaining the length of the active region of the element for an adequately narrow 20 MHz TE mode elevation beam width at 3 mm radially distant from the catheter, the element length should be approximately 0.5 mm long. The resulting half wave resonance frequency in LE mode then will be about 3 MHz. This design can be used for dual-mode imaging, but will not offer the focusing benefits that 10 MHz imaging can offer for the forward looking image planes. Other designs are possible, where the forward frequency is maintained near 10 MHz, but the required frequency for the side-looking mode will rise dramatically, and although this can be useful in itself, will complicate the design by requiring a concomitant increase in the number of elements and/or a reduction in the array element pitch dimension.

2. System Operation

The host processing system will control the array element selection and stepping process whereby one element, a two element pair, or other multiple elements in combination, will transmit and the same or other elements will receive the return echo information. The intended array operational mode is the LE resonant mode to send and receive echo information in a forward direction from the end of the catheter array. As stated earlier, the LE mode echoes produced may be isolated from the TE mode echoes through primarily frequency band limitations (both by transducer structural design and by electrical band selection filters), and through the beamforming reconstruction process itself as a kind of echo selection filter. To produce an image of the best possible in-plane resolution while operating in the forward-looking cross-sectional C-mode, the entire array diameter will be used as the maximum aperture dimension. This means that, in general, element echo sampling will take place at element locations throughout the whole array in preferably a sparse sampling mode of operation to gather the necessary minimum number of cross-product echoes needed to create image resolution of high quality everywhere in the reconstructed plane.

By using transmit-receive echo contributions collected from elements throughout the whole catheter array, using either a "complete data set" (e.g. 64×32), or a sparse sampling (e.g. less than 64×32) of elements as shown in FIGS. 10 and 11, the FWHM main beam resolution will be close to the 20 MHz resolution of the "side looking" cross-sectional image. This is due to the fact that although the "forward looking" echo frequency is about one half as much as the "side looking" frequency, the usable aperture for the forward looking mode is about 1.6 times that of the largest side looking aperture (i.e. the largest side looking aperture is about 0.7 mm, and the forward aperture is about 1.15 mm). For a 10 MHz forward looking design, the FWHM main lobe resolution in an image plane reconstructed at a depth of 3 mm will be approximately 0.39 mm, and 0.65 mm resolution at 5 mm distance.

Due to the limitation of beam diffraction available in the design using 10 MHz as the echo frequency for "forward looking", the C-mode image diameter that can be reconstructed and displayed with a high level of resolution from echo contributions throughout the whole array will be related to the distance between the reconstructed C-mode image plane and the distal end of the catheter. At 3 mm from the end of the catheter, the C-mode image diameter will be about 2.3 mm, at 5 mm distance the image diameter will be 4.6 mm, and at 7 mm distance the image diameter will be 6.9 mm.

Figure 16:
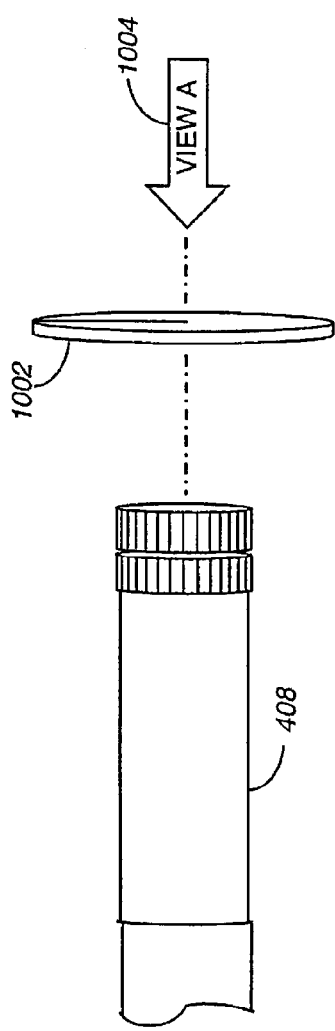
FIGS. 16 and 17 are diagrams showing the orientation of one C-mode image vector and a description of the initialization of the element stepping around the array.
Figure 17:
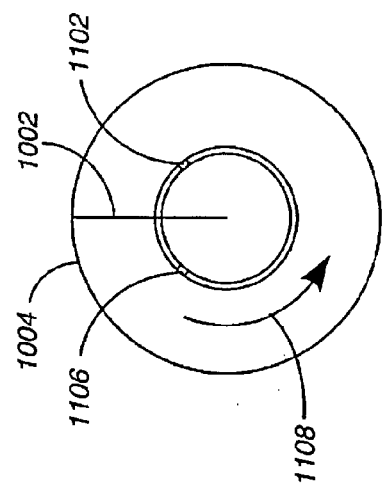

The host processing system, in addition to the control of the transducer element selection and stepping around the array, will control the transmit pulse timing, the use of any matched filter to perform echo pulse compression, and the echo band pass filter processing path in the system. The amplified and processed analog echo information is digitized with enough bits to preserve the dynamic range of the echo signals, and passed to the beam-former processing section. The beam former section uses stored echo data from the sparse array sampling (or alternatively the whole complete array echo data set of 64×32 of transmit-receive element pairs) that exist in an aperture of interest. As the element echo sampling continues sequentially around the circular array 1108 as shown in FIGS. 16 and 17, a number of "full trips" around the array will have been made to collect a sufficient number of echo cross-products (up to 105 in the preferred sparse sampling method) to allow the reconstruction of one image vector line 1102. As cross-product sampling continues around the array, the "older" echo cross-product collections are replaced with new samples and the next image vector is formed. This process repeats through an angular rotation to create new image vectors while sampling their element cross-product contributors around the array.

In FIG. 17, view "A" 1004 of FIG. 16 is shown which is a superposition of the distal catheter array and the forward looking image. Transducer elements #1 and #2 shown as item 1102 show the start location for the transmit (Tx) transducer elements. Transducer elements #12 and #13 shown as item 1106 is the start location for the Rx transducer elements. To collect the echo data for vector 1002, a total of 105 cross-products will be collected from all around the array. Rotation arrow 1108 shows the direction of Rx element stepping around the array. The Rx stepping preferably stops at about element #52 (e.g., 64−12=52). The stepping continues by stepping the Rx back around after the Tx has been incremented in the same "rotate" direction. Obviously, not all cross-product Tx-Rx terms are collected. Preferably, one takes the primary spatial frequencies, and continues the collection to limit the cross-products to 105.

In the same manner as described in the processing of the "side looking" image, the vector echo data is processed through envelope detection of the echo data and rejection of the RF carrier. Finally a process of coordinate conversion is done to map the radial vector lines of echo data to raster scan data for video display.

This processing system, through the host control, may also accomplish "forward looking" target (such as blood cells) velocity detection by either correlation-tracking the targets along the "forward looking" direction (with processing as earlier discussed with the "side looking" approach), or by standard Doppler processing of echo frequency shifts that correspond to target movement in directions parallel with the "forward looking" echo paths. The target (e.g. blood) velocity information may be displayed as a color on the video display; this velocity color information is superimposed on the image display to allow the user to see simultaneous anatomical information and target movement information.

Forward Looking Sagittal-Sectional B-Mode Operation

The advantage of the "forward looking" operation of the catheter imaging device is in its ability to see an image of objects in front of the catheter where possibly the catheter could not otherwise physically traverse. "Forward" B-mode plane imaging produces a cross-sectional planar "sector" view (see FIG. 3) that can exist in any plane parallel to the catheter central axis and distal to the end of the catheter array. This imaging mode may be used, in addition, to produce image "sector" views that are tilted slightly out of plane (see FIG. 3), and as well, may produce individual or sets of image "sectors" rotated generally about the catheter axis to allow the user to see a multitude of forward image slices in a format that shows clearly the multidimensional aspects of the forward target region of interest. This forward B-mode imaging (as with C-mode plane imaging) utilizes the ideal acoustic beam positioning for the detection and color image display of Doppler echo signals from targets moving generally in parallel with the long axis of the catheter device.

1. Transducer Operation

The transducer operation in creating the "forward looking" B-mode image format is virtually the same as discussed earlier for creating the "forward looking" C-mode image. The transducer in this "secondary" mode operates in the length extensional (LE) resonance, utilizing the k31 electromechanical coupling coefficient to describe the coupling efficiency. As with the C-mode image creation, the number of elements used at any time to form a wide beam pointing in the "forward" direction are selected to produce a required 60 degree FWHM beam width performance; the modal isolation techniques mentioned earlier against the higher frequency TE resonances are valid as well for this forward B-mode imaging method.

However, where it is merely preferred to operate the "forward" C-mode imaging with high bandwidth echo signals (low bandwidth echo signals can also be used, but with some minor loss in image resolution), it is a requirement in the "forward" B-mode imaging that only high bandwidth echo signals (echo fractional bandwidth greater than 30%) be used to preserve the "axial" resolution in the "forward" B-mode image. The lateral resolution in the "forward" B-mode image is determined (as the C-mode image plane resolution) by the aperture (diameter of the array) used for the image reconstruction. The lateral resolution performance will be as stated earlier (i.e. from the description of the C-mode imaging case) for various depths from the catheter distal end.

2. System Operation

The system operation in creating the "forward looking" B-mode image format is largely the same as discussed earlier for creating the "forward looking" C-mode image, with the difference being in the use of the echo signals collected in the beamforming process to create, rather than a C-mode image plane, a "forward" sagittal B-mode image in a plane that effectively cuts through the center of the circular array at the distal end of the catheter.

The host processing system as shown in FIG. 9, will control the array element selection and stepping process whereby one element, a two element pair, or other multiple elements in combination, will transmit and the same or other elements will receive the return echo information. The intended array operational mode is the LE resonant mode to send and receive echo information in a forward direction from the end of the catheter array. As stated earlier, the LE mode echoes produced may be isolated from the TE mode echoes through primarily frequency band limitations (both by transducer structural design and by electrical band selection filters), and through the beamforming reconstruction process itself as a kind of echo selection filter.

To produce an image of the best possible in-plane resolution while operating in the "forward looking" sagittal B-mode, the entire array diameter will be used as the maximum aperture dimension. This means that, in general, element echo sampling will take place at element locations throughout the whole array in preferably a sparse sampling mode of operation to gather the necessary minimum number of cross-product echoes needed to create image resolution of high quality everywhere in the reconstructed plane. By using transmit-receive echo contributions collected from elements throughout the whole catheter array, using either a "complete data set" (e.g. 64×32), or a sparse sampling (e.g. less than 64×32) of elements, the FWHM main beam lateral resolution in the B-mode plane will be close to the 20 MHz resolution of the "side looking" cross-sectional image. Similarly, as stated earlier for the C-mode image case, in the creation of the B-mode image using a 10 MHz forward looking design, the FWHM main lobe lateral resolution in the image plane reconstructed at a depth of 3 mm will be approximately 0.39 mm, and 0.65 mm resolution at 5 mm distance.

Due to the limitation of beam diffraction available in the design using 10 MHz as the echo frequency for "forward looking", the B-mode sector image width that can be reconstructed and displayed with a high level of resolution from echo contributions throughout the whole array will be related to the distance between the reconstructed B-mode target depth in the image sector and the distal end of the catheter. At 3 mm from the end of the catheter, the B-mode image sector width will be about 2.3 mm, at 5 mm distance the image sector width will be 4.6 mm, and at 7 mm distance the image sector width will be 6.9 mm.

The host processing system, in addition to the control of the transducer element selection and stepping around the array, will control the transmit pulse timing, the use of any matched filter to perform echo pulse compression, and the echo band pass filter processing path in the system. The amplified and processed analog echo information is digitized with enough bits to preserve the dynamic range of the echo signals, and passed to the beam-former processing section. The beam former section uses stored echo data from the sparse array sampling (or alternatively the whole complete array echo data-set of 64×32 of transmit-receive element pairs) that exist in an aperture of interest. As the element echo sampling continues sequentially around the circular array, a number of "full trips" around the array will have been made to collect a sufficient number of echo cross-products (up to 105 in the preferred sparse sampling method) to allow the reconstruction of one image vector line. As cross-product sampling continues around the array, the "older" echo cross-product collections are replaced with new samples and the next image vector is formed. This process repeats through an angular rotation in the array to create new image vectors while sampling their element cross-product contributors around the array.

The method used for the creation of a single "forward looking" sagittal B-mode image plane may be expanded to create multiple rotated sagittal planes around an axis either congruent with the catheter central axis, or itself slightly tilted off the catheter central axis. If enough rotated planes are collected, the beamforming system could then possess a capability to construct and display arbitrary oblique "slices" through this multidimensional volume, with B-mode or C-mode visualization in either a 2-D sector format, a 2-D circular format, or, other multidimensional formats. The echo data volume may also be off-loaded to a conventional 3-D graphics engine that could create the desired image format and feature rendering that would enable improved visualization. In the same manner as described in the processing of the "forward looking" C-mode image, the vector echo data is processed through envelope detection of the echo data and rejection of the RF carrier. Finally a process of coordinate conversion is done to map the radial vector lines of echo data to a video sector-format display of the "forward looking" B-mode image.

This processing system, through the host control, may also accomplish "forward looking" target (such as blood cells) velocity detection by either correlation-tracking the targets along the "forward looking" direction (with processing as earlier discussed with the "side looking" approach), or by standard Doppler processing of echo frequency shifts that correspond to target movement in directions parallel with the "forward looking" echo paths in the "forward looking" B-mode plane. The target (e.g. blood) velocity information may be displayed as a color on the video display; this velocity color information is superimposed on the image display to allow the user to see simultaneous anatomical information and target movement information.

The invention has a number of important features and advantages. It provides an ultrasonic imaging transducer and method that can be used for imaging tissue in multiple planes without any moving parts. It can operate in both forward and side imaging modes, and it permits imaging to be done while procedures are being carried out. Thus, for example, it can operate in a forward looking C-mode, while at the same time a therapeutic device such as a laser fiber-bundle can be used to treat tissue (e.g. an uncrossable arterial occlusion) ahead of the catheter tip either by tissue ablation, or, tissue photochemotherapy. The laser pulses may be timed with the ultrasound transmit-receive process so that the high frequency laser induced tissue reverberations can be seen in the ultrasound image plane simultaneously. In this way the invention can dynamically guide the operator's vision during a microsurgical procedure.

The invention also encompasses methods of using the provided device to image an object in a forward direction. The method may involve providing a forward imaging device comprising an elongated body configured to fit within the lumen of a vessel and at least one imaging sensor located on the elongated body configured to image an object in a forward direction. The method may further involve inserting the device into a lumen of a vessel, and imaging an object in a forward direction. The device of the provided method has already been described in great detail above.

In practice, the method may also involve injecting a local anesthetic into the skin to numb the area of the patient prior to surgery. A puncture is then made with a needle in either the femoral artery in the groin or the radial artery in the wrist before a guidewire is inserted into the arterial puncture. A plastic sheath (with a stiffer plastic introducer inside it) is then threaded over the wire and pushed into the artery. The method may further involve inserting the provided forward looking catheter over the provided guidewire and advancing the catheter towards the heart. Once the catheter is in place, it can be used image the area, including imaging in a forward direction. The provided catheter may also be used to perform a number of procedures including angioplasty, PCI (percutaneous coronary intervention) angiography, balloon septostomy, and an Electrophysiology study or ablation procedure.

The present invention can also be used in a biopsy or atherectomy procedure to allow the operator to perform a tissue identification prior to tissue excision; the advantage being that the catheter or biopsy probe device can be literally pointing in the general direction of the target tissue and thus aid significantly in the stereotaxic orientation necessary to excise the proper tissue sample. The invention can also be used for the proper positioning of a radiotherapy core wire in the treatment of target tissue that exists well beyond the distal extent of the catheter.

It is apparent from the foregoing that a new and improved ultrasonic imaging is device and method have been provided. While only certain presently preferred embodiments have been described in detail, as will be apparent to those familiar with the art, certain changes and modifications can be made without departing from the scope of the invention as defined by the following claims.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A forward imaging device for imaging the inside of a vessel, the device comprising:
   an elongated body comprising a distal tip; and
   at least one optical-acoustic imaging sensor located at the distal tip of the elongated body and configured to image an object in a forward direction,
   wherein the at least one optical-acoustic imaging sensor comprises an optical fiber and a photoacoustic material located at the distal tip of the elongated body, wherein the optical fiber comprise a curved portion with a blazed fiber Bragg grating located at the distal tip of the elongated body, the curved portion configured such that the blazed fiber Bragg grating transmits optical energy towards the photoacoustic material.

2. The device of claim 1, wherein the elongated body is a catheter.

3. The device of claim 1, wherein the elongated body is a guidewire.

4. The device of claim 1, further comprising at least one imaging sensor configured for oblique imaging and located at a side region of the elongated body.

5. The device of claim 1, further comprising a pressure sensor located on the elongated body.

6. A method for imaging an object in a forward direction, the method comprising:
   providing a forward imaging device comprising an elongated body comprising a distal tip and configured to fit within a lumen of a vessel and at least one optical-acoustic imaging sensor located at the distal tip of the elongated body configured to image an object in a forward direction, wherein the at least one optical-acoustic imaging sensor comprises an optical fiber, the optical fiber comprising a curved portion with a blazed fiber Bragg grating, the curved portion located at the distal tip of the elongated body and configured such that the blazed fiber Bragg grating transmits optical energy towards a photoacoustic material also located at the distal tip of the elongated body;
   inserting the device into a lumen of a vessel; and
   imaging an object in a forward direction.

* * * * *